Figure 1:
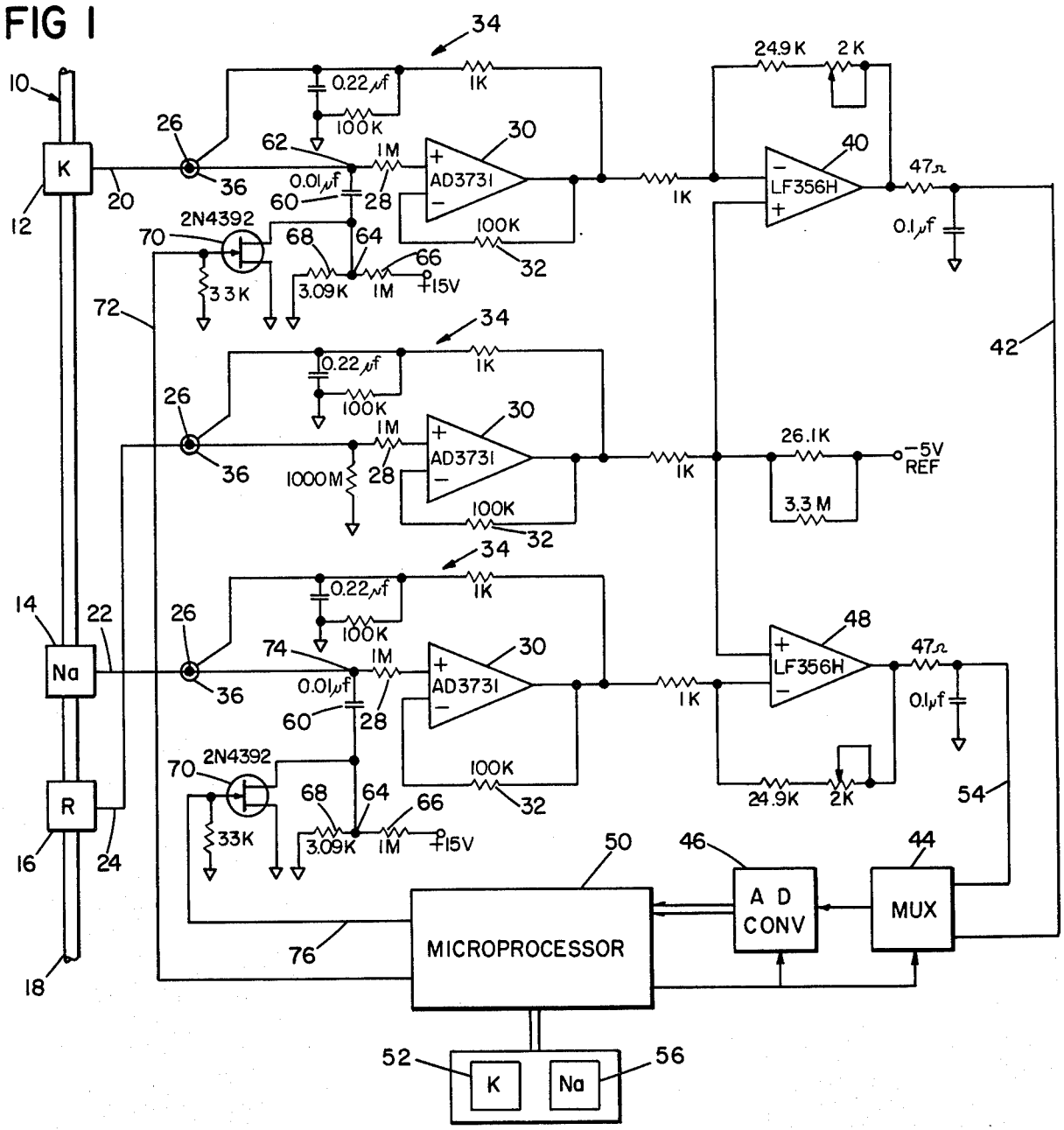

United States Patent [19]

Rolfe

[11] Patent Number: 4,468,608
[45] Date of Patent: Aug. 28, 1984

[54] ELECTROCHEMICAL SENSOR INSTRUMENTATION

[75] Inventor: Norman F. Rolfe, Carlisle, Mass.

[73] Assignee: Instrumentation Laboratory Inc., Lexington, Mass.

[21] Appl. No.: 329,747

[22] Filed: Dec. 11, 1981

[51] Int. Cl.³ .............................................. G01R 31/02
[52] U.S. Cl. ...................................... 324/51; 204/401
[58] Field of Search ............... 324/51, 65 R; 204/1 T, 204/401

[56] References Cited

U.S. PATENT DOCUMENTS

| | | | |
|---|---|---|---|
| 2,117,596 | 5/1938 | Bender | 204/5 |
| 2,563,062 | 8/1951 | Perley | 204/195 |
| 2,913,386 | 11/1959 | Clark | 204/195 |
| 3,111,622 | 11/1963 | Zechter | 324/57 |
| 3,661,748 | 5/1972 | Blackmer | 204/195 |
| 3,713,020 | 1/1973 | Kohler | 324/51 |
| 3,718,568 | 2/1973 | Neuwelt | 204/195 |
| 3,986,108 | 10/1976 | Thomas | 324/60 |
| 4,189,367 | 2/1980 | Connery | 204/195 |
| 4,223,549 | 9/1980 | Kitzinger | 204/401 X |

FOREIGN PATENT DOCUMENTS 1018877  2/1966  United Kingdom.

Primary Examiner—Stanley T. Krawczewicz

[57] ABSTRACT

An electrochemical sensor system includes a high impedance ion selective electrode and an electrode test circuit that has an isolation capacitor connected between the output signal lead from the ion selective electrode and a test voltage terminal, and a monitoring circuit connected to respond to the output signal from the electrode. The isolation capacitor is a high quality capacitor and provides a shunt impedance that is much higher than the maximum electrode impedance. A voltage transition at the test voltage terminal is coupled by the isolation capacitor to the output lead and the resulting decay rate of the voltage transition on the output lead is monitored to provide an indication of the quality of the electrode.

6 Claims, 2 Drawing Figures

ELECTROCHEMICAL SENSOR INSTRUMENTATION

This invention relates to electrochemical sensor instrumentation and more particularly to instrumentation of the type which includes ion selective electrodes.

Analysis systems employing ion selective electrochemical electrodes are useful for measurement of concentration of ions of hydrogen, sodium, potassium, and the like. Such analysis systems may be used, for example, to measure particular constituents of a blood sample (whole blood, blood serum, or plasma) and provide diagnostic information on metabolic disturbances, assist in control of life support devices or evaluate the effectiveness of therapeutic measures. In such systems, the sample to be analyzed is drawn or injected into an analysis chamber for exposure to an ion selective membrane (of glass or plastic material, for example) and the magnitude of the electrical potential developed at the sample-membrane interface (which is related to the ionic concentration of the constituent of interest in the sample being analyzed) is measured. Various techniques have been proposed for testing such electrodes to determine whether the ion selective membrane is damaged or whether the output impedance of the electrode has drifted out of specification; such techniques including circuits in which unidirectional test currents are passed through the membrane, and circuits which use an AC current to monitor the impedance of the electrode.

In accordance with the invention there is provided an electrochemical sensor system that includes a high impedance ion selective electrode and an improved electrode test circuit with an isolation capacitor connected between the output signal lead from the ion selective electrode and a test voltage terminal. A monitoring circuit is connected to respond to the output signal from the electrode. The isolation capacitor is a high quality capacitor and provides a shunt impedance that is much higher than the maximum electrode impedance; its impedance preferably being at least one hundred gigaohms. Teflon and polystyrene type capacitors are suitable. A voltage transition at the test voltage terminal is coupled by the isolation capacitor to the output lead and the resulting decay rate of the voltage transition on the output lead is monitored to provide an indication of the quality of the electrode.

The invention allows testing of the ion selective electrode with test circuitry that is isolated from the measurement circuit by the isolation capacitor. The voltage transition (preferably a step transition) may be obtained with the use of an inexpensive switch, in contrast with high impedance low leakage switches used in prior art systems where the bulk resistance of an ion selective electrode membrane was measured by passing a test current through the membrane.

In a particular embodiment, the system includes sodium and potassium sensing electrodes, each of which has a nominal impedance of over five hundred megohms, and a reference electrode assembly. Similar test circuits are associated with the sodium and potassium electrodes and each test circuit includes a test voltage source in the form of a voltage divider and an FET switch which shunts a portion of the voltage divider in an arrangement in which operation of the switch is effective to apply a step voltage to the isolation capacitor. The system also includes control circuitry which operates the switch and monitors the resulting change in output voltage on the electrode output line. That output voltage decays at a rate that is a function of the value of the isolation capacitor and the resistance of the ion-selective electrode and is appropriately monitored, for example, by sampling at periodic intervals or by periodic comparisons of that voltage with a threshold value. In a particular embodiment, a positive 45 millivolt step is applied to the isolation capacitor and the resulting voltage is sampled ten milliseconds and one second after the step voltage is applied to determine whether the electrode is within lower and upper specification limits.

Figure 2:
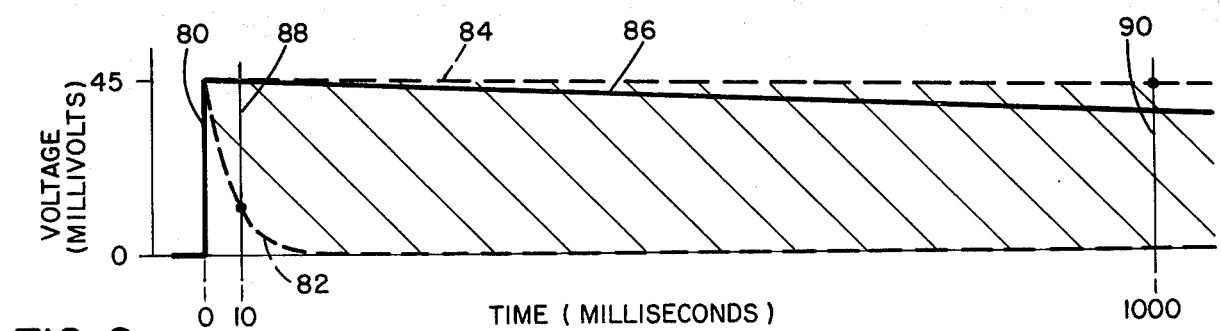

The invention provides reliable electrochemical sensor system monitoring circuitry in simple, inexpensive, and reliable arrangements. Other features and advantages of the invention will be seen as the following description of a particular embodiment progresses, in conjunction with the drawing, in which:

FIG. 1 is a schematic diagram of an electrochemical sensor system in accordance with the invention; and FIG. 2 is a diagram illustrating change in output voltage in response to application of a positive step voltage to the isolation capacitor of the test circuit.

DESCRIPTION OF PARTICULAR EMBODIMENT

The analysis system shown in FIG. 1 includes a sample flow line 10 that extends through potassium sensing electrode system 12, sodium sensing electrode system 14, and reference electrode system 16 to outlet 18. Details of electrode systems 12, 14, and 16 may be had with reference to copending application Ser. No. 175,053 filed Aug. 4, 1980, entitled Analysis System, which application is assigned to the same assignee as this application and is hereby incorporated herein by reference. Each electrode system 12, 14, and 16 has an output over a corresponding line 20, 22, 24 to a corresponding shielded plug connector 26. A buffer amplifier 30 is connected to the output of each electrode via plug connection 26 and resistor 28. Each buffer amplifier circuit includes a feedback resistor 32 and a drive connection 34 to the shield 36 of each plug connection 26 to limit the effect of shield capacitance.

Connected to the outputs of potassium electrode and reference electrode buffer amplifiers 30 is a differential amplifier 40 which provides an output over line 42 through multiplexer 44 and A-D convertor 46 to microprocessor 50 which responds to that output to produce on digital display 52 an indication of the potassium value being measured by electrode 12. A similar differential amplifier circuit 48 has inputs from sodium electrode and reference electrode buffer amplifiers 30 and provides an output on line 54 to microprocessor 50 which similarly provides an indication of the measured sodium value on display 56.

Connected to the output signal line 20 from the potassium electrode 12 (between plug connection 26 and resistor 28) is a test circuit that includes a high quality 0.01 microfarad polystyrene isolation capacitor 60 (500 gigaohm shunt impedance) that has one terminal connected to the output signal line at junction 62 and its other terminal connected to junction 64 of a voltage divider network that includes resistors 66 and 68. Also connected to junction 64 is a normally closed FET switch 70 that has a control input over line 72 from microprocessor 50. A similar test circuit is connected to output signal line 22 of sodium electrode 14 at junction 74 and its switch 70 is similarly controlled in response to a signal on line 76 from microprocessor 50.

When it is desired to test the potassium electrode 12 (which includes an ion selective membrane of synthetic polymeric material), microprocessor 50 generates a signal on line 72 to open switch 70, producing a 45 millivolt voltage step 80 (FIG. 2) which is applied through isolation capacitor 60 to junction 62. In this embodiment, the minimum acceptable resistance of potassium electrode 12 is one megohm and its maximum acceptable resistance is 800 megohms. The lower and upper specification limits, in terms of the test voltage step 80, are indicated at 82 and 84 respectively in FIG. 2. With the application of the step voltage 80 of known value, a voltage change appears on line 20 which decays exponentially as indicated at 86 in FIG. 2. Microprocessor 50 samples the change in voltage on line 42, ten milliseconds and one second after switch 70 is opened. In this embodiment, if the electrode resistance is one megohm, the voltage on line 20 would decay as indicated at 82 in FIG. 2, and will be 16.5 millivolts ten milliseconds after switch 70 is opened (time 88). Should the voltage at that time be less than 16.5 millivolts, the resistance of the potassium electrode system is less than the predetermined minimum value for an intact electrode system, and microprocessor 50 generates an output indicating a defective electrode. Similarly, if the electrode system has a much higher resistance, the exponential decay will be much slower, as indicated at line 84. Microprocessor 50 also samples line 20 one second after switch 70 is opened (time 90). If the voltage at that time exceeds 39.7 millivolts, electrode system 12 has a resistance in excess of 800 megohms, and microprocessor 50 indicates that the electrode system 12 has a resistance greater than the predetermined maximum value.

Microprocessor 50 periodically opens switch 70 to test potassium electrode. Between testing intervals, constituent measurements by the potassium electrode are processed and results are generated on display 52.

Sodium electrode 14, which employs a glass membrane, is similarly tested in response to a signal from microprocessor on line 76 and sampling of the resulting voltage on line 54. In a particular embodiment, the sodium electrode has a minimum resistance of one megohm (corresponding to a voltage of +16.5 millivolts ten milliseconds after its switch 70 is open) and a maximum resistance of 700 megohms (corresponding to a voltage of 39 millivolts one second after its switch 70 is opened).

The procedures described above as being executed by microprocessor 50 can of course be executed by other types of controllers with the voltage on the output line 42 (54) being appropriately continuously monitored or sampled at periodic or at chosen intervals after application of the step voltage 80 to the test junction 62 (74). The exponential decay rate of the voltage on the output line 20 (22) is a function of the value of the high quality isolation capacitance 60 and the resistance of the electrode 12 (14). The resulting rate of exponential decay of the output voltage indicates whether the output impedance of the electrode under test is within predetermined limits, as indicated by the shaded area of FIG. 2.

While a particular embodiment of the invention has been shown and described, various modifications thereof will be apparent to those skilled in the art, and therefore it is not intended that the invention be limited to the disclosed embodiment or to details thereof and departures may be made therefrom within the spirit and scope of the invention.

What is claimed is:

1. In an analytical system that employs an ion selective electrode for measuring a constituent of a fluid, apparatus for testing the ion selective electrode to determine if its output impedance is within predetermined limits comprising
    circuitry for applying a signal transition to the output signal line of said ion selective electrode, and
    means for monitoring the exponential decay rate of the signal on said output line resulting from said applied signal transition for indicating a faulty ion selective electrode as a function of the exponential decay rate of said resulting output signal.

2. In an analytical system that employs an ion selective electrode for measuring a constituent of a fluid, apparatus for testing the ion selective electrode to determine if its output impedance is within predetermined limits comprising
    a high quality capacitor whose shunt impedance is much higher than the maximum electrode impedance, means connecting one terminal of said capacitor to the output signal line of said ion selective electrode,
    means for applying a step voltage to the other terminal of said capacitor to apply a signal transition to said output signal line of said electrode, and
    means for monitoring the exponential decay rate of the signal on said output line resulting from said applied step voltage for indicating a faulty ion selective electrode as a function of the exponential decay rate of the signal on said electrode output signal line.

3. The apparatus of claim 2 wherein said signal transition applying circuitry includes a voltage divider network connected to said other terminal of said capacitor, and a switch shunting one component of said voltage divider network.

4. The apparatus of claim 3 wherein said switch is normally closed and shunts a resistor component of said voltage divider network connected between said capacitor and ground.

5. Circuitry for monitoring a high impedance ion selective electrode that provides an output signal over an output signal line comprising a capacitor coupled to said output signal line of said ion selective electrode, the shunt impedance of said capacitor being at least one hundred gigaohms, means to apply a step voltage to said capacitor, and means to monitor the change in voltage on said output signal line resulting from the application of said step voltage to said capacitor to provide an indication of the quality of said ion selective electrode.

6. The apparatus of claim 2, 4 or 5 and further including a buffer amplifier connected to said electrode output signal line, a reference electrode and associated buffer amplifier for sensing the fluid monitored by said ion selective electrode, a differential amplifier that responds to the output signals from the buffer amplifiers of said ion selective and reference electrodes and wherein said monitoring means samples the output signal from said differential amplifier at predetermined time intervals after said step voltage is applied to said capacitor to provide an indication whether the resistance of said ion selective electrode is within preestablished upper and lower limits.

* * * * *